United States Patent [19]

Haber et al.

[11] Patent Number: 5,374,249

[45] Date of Patent: Dec. 20, 1994

[54] PHARMACEUTICAL MIXING CONTAINER WITH COMBINATION STOPPER AND PUMP

[75] Inventors: Terry M. Haber, Lake Forest; Clark B. Foster, Laguna Niguel; William H. Smedley, Lake Elsinore, all of Calif.

[73] Assignee: Habley Medical Technology Corporation, Laguna Hills, Calif.

[21] Appl. No.: 949,600

[22] Filed: Sep. 23, 1992

[51] Int. Cl.$^5$ .................................. A61M 37/00
[52] U.S. Cl. ........................ 604/91; 604/89; 604/82; 604/56; 604/416
[58] Field of Search .............. 604/43, 45, 56, 82, 604/89–92, 148, 416

[56] References Cited

U.S. PATENT DOCUMENTS

| | | | |
|---|---|---|---|
| 3,164,303 | 1/1965 | Trautmann | 604/92 |
| 3,464,412 | 9/1969 | Schwartz | 604/89 |
| 3,659,749 | 5/1972 | Schwartz . | |
| 3,678,931 | 7/1972 | Cohen . | |
| 3,682,174 | 8/1972 | Cohen | 604/90 |
| 4,116,240 | 9/1978 | Guiney | 604/91 |
| 4,493,348 | 1/1985 | Lemmons . | |
| 4,563,174 | 1/1986 | Dupont et al. | 604/89 |
| 4,850,966 | 7/1989 | Grau et al. . | |

Primary Examiner—Jerome L. Kruter
Assistant Examiner—P. Zuttarelli
Attorney, Agent, or Firm—Townsend & Townsend Khourie & Crew

[57] ABSTRACT

A pharmaceutical mixing container for storing a liquid having at least two factions which tend to separate during storage. A housing has an inner volume and is closed at one end by a septum arrangement and at another end by a combination sealing and pumping member. The combination sealing and pumping member has an integrally formed outer diaphragm element forming a diaphragm chamber with the inner structure of this element, and a plurality of fluid channels extending through the sealing and pumping element from the diaphragm chamber to the surface facing the inner volume of the container. A driving member assembly is coupled to the diaphragm element to enable this element to be extended and retracted by manipulating the driving element assembly inwardly and outwardly of the container. Operation of the diaphragm element provides a reversible gentle fluid flow enabling the liquid and other constituents of the pharmaceutical to be drawn into the diaphragm chamber and expelled back into the inner volume of the container, thereby thoroughly admixing the constituents.

5 Claims, 2 Drawing Sheets

PHARMACEUTICAL MIXING CONTAINER WITH COMBINATION STOPPER AND PUMP

BACKGROUND OF THE INVENTION

This invention relates to containers for liquids having a miscible component. More particularly, this invention relates to mixing containers for storing a liquid pharmaceutical.

Containers are known for storing a pharmaceutical having a liquid component and a second component miscible with a liquid component. A typical container of this type is filled with the pharmaceutical and stored for later use. Some pharmaceuticals separate into their individual components when left in storage. For example, liquid NPH insulin has a crystalline faction which must be in solution in order to be effectively administered. During storage in a container, such crystals precipitate out of the liquid solution and must be thoroughly mixed with the liquid faction just prior to administration. Admixture of the crystalline faction and the liquid faction has been achieved in the past in a number of different ways. One such technique is to provide a mixing element which is freely moveable within the container, in a similar manner to the mixing ball found in ordinary aerosol spray cans. This solution has been found to be less than desirable, since the crystalline faction is composed of delicate crystals which should not be mechanically damaged or ruptured during the mixing process. The use of a freely moveable mixing element within the container, however, has been found to damage and rupture the crystals, which severely impairs the effectiveness of the pharmaceutical. Efforts in the past to provide a pharmaceutical mixing container devoid of the above disadvantage have not been successful to date.

SUMMARY OF THE INVENTION

The invention comprises a pharmaceutical mixing container which provides thorough admixing of separated components in a pharmaceutical without mechanically damaging those components.

A pharmaceutical mixing container for storing a liquid having at least two miscible components includes a housing having a first end, a second end and a wall structure defining an inner volume, the housing preferably having cylindrical geometry. A closure member providing a fluid seal is arranged at the first end of the housing, the closure member preferably including a septum and a retaining band for securing the septum to the first end of the housing. A combination sealing and pumping member is positioned at least partially within the housing, preferably adjacent the second end. This member provides both a second fluid seal for containing the liquid within the housing and a pumping action for admixing the liquid faction and other constituents of a pharmaceutical contained within the inner volume of the container. The sealing and pumping member is an integrally formed body having an inner surface exposed to the inner volume of the container, a diaphragm element accessible to an externally located actuating element, the diaphragm element defining an inner diaphragm chamber, and at least one fluid communication channel extending from the diaphragm chamber to the inner volume of the container.

The actuating element preferably includes an inner driving element and an outer driving element, with the inner driving element having a diaphragm element gripping end coupled to the diaphragm element. The inner driving element also includes a central body portion which is slidably received within the hollow interior of an outer driving element terminating in a base portion, which provides a limit stop for relative motion between the inner driving element and the outer driving element.

In use, the liquid is stored within the container and is admixed prior to administration by actuating the diaphragm element with the actuating element. During motion of the diaphragm, liquid is drawn into the diaphragm chamber via the fluid channel, while during inward motion of the diaphragm element outwardly from the housing element this same liquid is expelled back into the inner volume of the container. This pumping action causes gentle turbulent currents to be generated within the inner volume of the container, which results in thorough admixing of the pharmaceutical constituents. Since the magnitude of the pumping flow is controlled by the user, mechanical damage to the constituents being admixed is minimized or eliminated by manipulating the diaphragm element at a gentle pace.

The liquid may be hydraulically withdrawn from the inner volume of the housing by penetrating the system with a needle cannula of a syringe and subsequently operating the syringe. The liquid may also be expelled from the inner volume of the container housing by penetrating the septum with a double point needle and forcibly ejecting the liquid by using the actuating element to drive the combination sealing and pumping element in the direction of the septum end of the housing.

While the invention may be employed with a wide variety of miscible pharmaceutical components, it is ideally suited for use with pharmaceuticals having a liquid faction and a crystalline faction requiring admixture prior to use. In particular, the manually controllable gentle turbulence afforded by the reversible pumping flow is sufficient to thoroughly admix the constituents without damaging the crystal structure.

For a fuller understanding of the nature and advantages of the invention, reference should be had to the ensuing detailed description taken in conjunction with the accompanying drawings.

DESCRIPTION OF THE PREFERRED EMBODIMENTS

Figure 1:
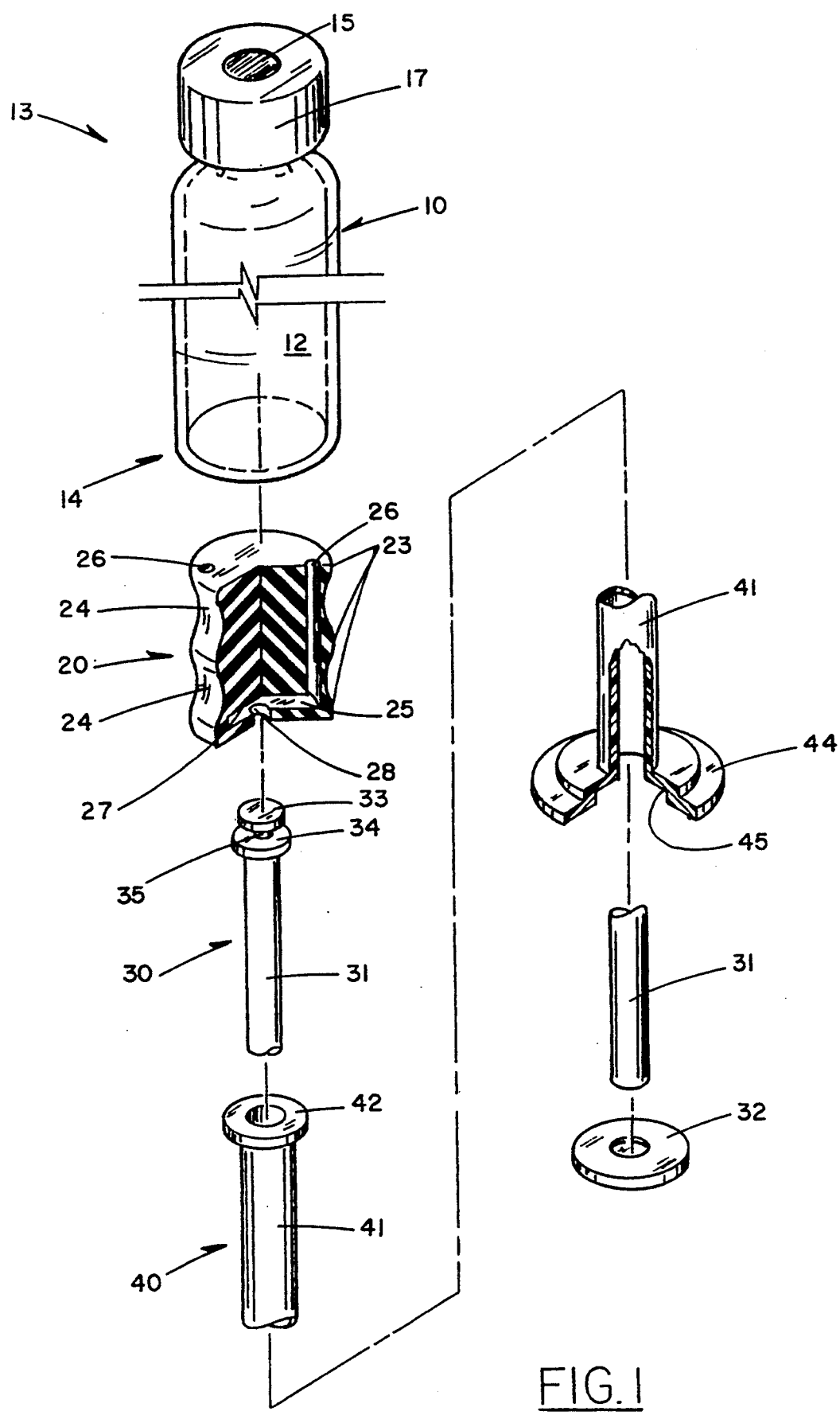
FIG. 1 is an exploded perspective view showing a first embodiment of the invention.
Figures 2, 3:
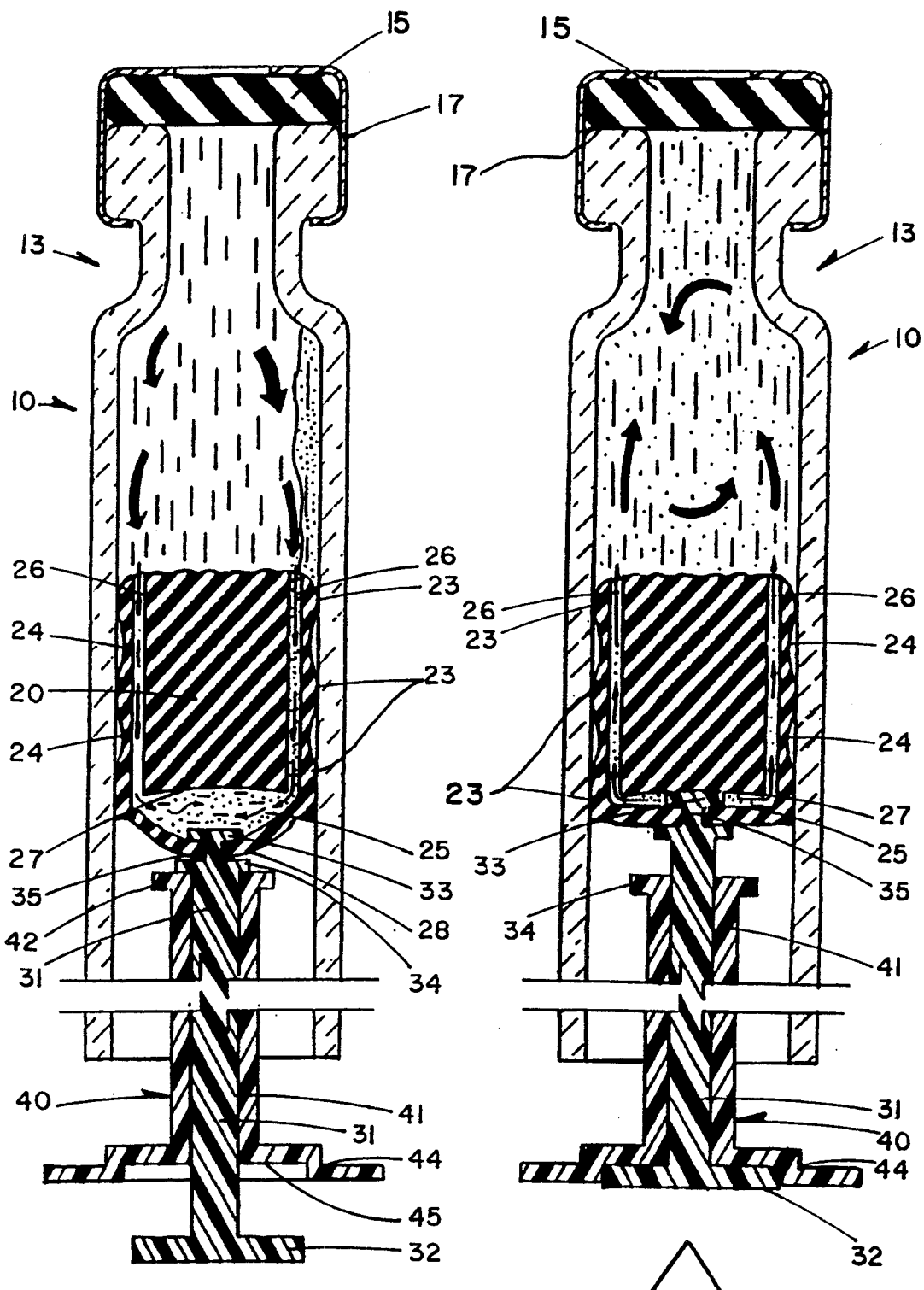
FIG. 2 is a sectional view of the assembled device showing the pump diaphragm fully extended.
FIG. 3 is a sectional view of the assembled device showing the pump diaphragm fully relaxed.

Turning now to the drawings, FIGS. 1–3 illustrate the preferred embodiment of the invention. As seen in these Figs., a cartridge housing generally designated with reference numeral 10 has a generally cylindrical geometrical configuration defining an inner volume 12, a distal end 13 and a proximal end 14. Housing 10 may be fabricated from glass or any suitable plastic material which is compatible with the pharmaceutical to be contained therewithin. Secured to distal end 13 is a closure member comprising an elastomeric septum 15 (FIG. 2) which is retained to first end 13 by means of a metal band 17. Septum 15 and band 17 are fabricated and arranged in such a manner that access to the inner volume 12 may be gained by penetrating the band 17 and septum 15 with a needle-like probe, such as a needle cannula of a syringe or a double-point syringe needle.

A combination sealing member and pump 20 having an outer diameter providing a sealing engagement with the inner walls of cartridge housing 10 is installed adjacent the proximal end 14 of cartridge housing 10. Member 20 may be fabricated from a wide variety of suitable materials, such as butyl rubber, silicone rubber or the equivalent. Member 20 functions in part to provide a slidable fluid seal for the proximal end of inner volume 12. For this purpose, member 20 is provided with a plurality of crests 23 and troughs 24 along the outer surface thereof.

Member 20 also functions in part to provide gentle hydraulic pumping action for the liquid contained within inner volume 12 so that the liquid faction can be thoroughly admixed with the remaining constituents. To this end, member 20 is provided with an integral diaphragm element 25 at the bottom thereof, and a plurality (two illustrated) of Channels 26 for providing fluid communication between inner volume 12 and a diaphragm chamber formed in the volume between the diaphragm element 25 and the lower internal surface 27 of member 20. Diaphragm element 25 is provided with a connection aperture 28 for the purpose described below.

A diaphragm actuating assembly includes an inner drive member generally designated with reference numeral 30 and an outer drive member generally designated with reference numeral 40. Inner drive member 30 includes a longitudinally extending main body portion 31, illustrated as a cylindrical member, a lower stop member 32 illustrated as a disk, and an upper actuating end comprising a pair of axially spaced diaphragm gripping elements 33, 34 axially separated by a narrow diameter connecting element 35. As best depicted in FIGS. 2 and 3, the outer diameter of connecting element 35 is substantially equal to the inner diameter of lower diaphragm aperture 28. The outer diameter of upper gripping element 33 is sufficiently small to permit this element to be maneuvered through diaphragm element aperture 28, while being sufficiently large to prevent ready passage through the aperture 28 when the diaphragm element 25 is manipulated in the manner described below.

Outer drive member 40 has a longitudinally extending central body portion 41 having a hollow interior sized to slidingly accommodate the outer surface of the central body portion 31 of inner drive member 30. Outer drive member 40 is provided with an upper end collar 42 of enlarged diameter and a lower base member 44 having a central recess 45 sized to accommodate element 32 of inner drive member 30 in the manner best illustrated in FIG. 3. Both inner drive member 30 and outer drive member 40 are preferably fabricated from suitable plastic material, such as polystyrene, polycarbonate and acrylic.

To assemble, the upper gripping element 33 of inner drive member 30 is maneuvered through aperture 28 in diaphragm element 25 until element 33 is fully received within the diaphragm chamber. Thereafter, outer drive member 40 is maneuvered over body portion 31 of inner drive member 30, after which lower stop member 32 is attached to the lower end of main body portion 31 of inner drive member 30. Thereafter, the assembly comprising elements 20, 30 and 40 is inserted into the interior of container 10 to seal the container 10 and provide the inner volume 12. The inner volume 12 is then filled with the pharmaceutical liquid, and septum 15 and closure band 17 are installed to seal volume 12.

When the pharmaceutical is to be administered, the user grasps the base 44 of outer drive member 40 with one hand and the lower stop member 32 of the inner drive member 30 with the other hand. Next, the inner drive member is withdrawn relative to the outer drive member so that the diaphragm element 25 is extended in the manner illustrated in FIG. 2, thereby enlarging the diaphragm chamber. This outward movement of the diaphragm element 25 draws the liquid into the channels 26 and into the diaphragm chamber along with the other constituents of the pharmaceutical. Next, the user drives the inner drive member in the upward direction while maintaining the outer drive member relatively stationary to maneuver the diaphragm element 25 to the fully relaxed position illustrated in FIG. 3. As the diaphragm element 25 is driven upwardly, the mixture of liquid and other pharmaceutical constituents is driven upwardly through the channels 26 into the inner volume 12. By gently repeating this process, the pharmaceutical ingredients are thoroughly admixed without mechanically damaging any delicate constituents, such as the crystalline faction found in NPH type insulin. As suggested by the liquid flow arrows shown in FIGS. 2 and 3, the pumping action generates gentle turbulent currents within the liquid in inner volume 12 to assist in the mixing process.

After thorough admixture, the septum 15 is penetrated by means of a needle cannula of a syringe or a double point needle, and the liquid is withdrawn from inner volume 12 either hydraulically or by pushing inner and outer drive members 30, 40 against member 20 so as to translate member 20 in the direction of distal end 13 of cartridge housing 10.

As will now be apparent, the invention provides a pharmaceutical mixing container capable of thoroughly admixing the pharmaceutical constituent ingredients in a relatively simple and expedient fashion. In addition, mixing containers fabricated according to the invention are relatively simple and inexpensive to fabricate, can be readily filled with the appropriate liquid pharmaceutical, and can easily be employed for administering the pharmaceutical to a patient.

While the above provides a full and complete disclosure of the preferred embodiments of the invention, various modifications, alternate constructions and equivalents may occur to those skilled in the art. For example, while the member 20 has been illustrated as having a pair of mixing channels 26, a greater number of channels may be employed, if desired. In addition, member 20 may be arranged as a stationary, as opposed to slidable, member within container 10. Further, in some applications it may be desirable to provide a bias spring or the equivalent between the lower stop member 32 and the lower base member 44 to bias the inner drive member 30 to a rest position in which the lower surface of gripping element 34 contacts the upper surface of collar 42. In such an alternate arrangement, pumping action can be initiated by pulling down on base member 44, to draw diaphragm element 25 outwardly of housing 10, followed by alternate pressing and releasing of stop member 32. When the stop member 32 is released, the bias spring returns the inner drive member to the rest position. This arrangement permits the pumping flow to be generated with one hand while the other hand grasps the container housing 10. Therefore, the above descriptions and illustrations should not be construed as limiting the scope of the invention, which is defined by the appended claims.

What is claimed is:

1. A pharmaceutical mixing container for storing a liquid with a miscible component, said container comprising:

a housing having a first end, a second end and a wall structure defining an inner volume;

a closure member at said first end providing a fluid seal;

combination sealing and pumping means positioned between said first end and said second end for providing a second fluid seal so that said inner volume is closed and for providing a reversible pumping flow for fluid within said inner volume; and means for actuating said combination sealing and pumping means to provide said reversible pumping flow to admix any liquid and miscible components contained within said inner volume, said combination sealing and pumping means comprising an integral member having a first surface exposed to said inner volume, a diaphragm member adapted to be coupled with said actuating means, an internal volume defined in part by said diaphragm member and forming a diaphragm chamber, and a fluid channel for providing fluid communication between said diaphragm chamber and said inner volume via said first surface.

2. The invention of claim 1 wherein said actuating means includes an inner drive member having a gripping end coupled to said diaphragm member for enabling said diaphragm member to be manually extended and relaxed to provide said pumping flow.

3. The invention of claim 1 wherein said combination sealing and pumping means is slidably arranged within said housing so that said actuating means is capable of translating said combination sealing and pumping means to expel liquid from said inner volume when said closure member is opened.

4. A pharmaceutical mixing container for storing a liquid with a miscible component, said container comprising:

a housing having a first end, a second end and a wall structure defining an inner volume;

a closure member at said first end providing a fluid seal;

combination sealing and pumping means positioned between said first end and said second end for providing a second fluid seal so that said inner volume is closed and for providing a reversible pumping flow for fluid within said inner volume, said combination sealing and pumping means comprising an integral member having a first surface exposed to said inner volume, a diaphragm member adapted to be coupled with said actuating means, an internal volume defined in part by said diaphragm member and forming a diaphragm chamber, and a fluid channel for providing fluid communication between said diaphragm chamber and said inner volume via said first surface; and means for actuating said combination sealing and pumping means to provide said reversible pumping flow to admix any liquid and miscible components contained within said inner volume, said actuating means including an inner drive member having a gripping end coupled to said diaphragm member for enabling said diaphragm member to be manually extended and relaxed to provide said pumping flow and an outer driving member having a central aperture for slidably receiving at least a portion of said inner driving member and a base member for providing a limit stop for sliding motion of said inner drive member in the direction of said inner volume.

5. The invention of claim 4 wherein said actuating means further includes means for biasing said inner drive member with respect to said outer drive member in a direction outwardly of said inner volume.

* * * * *